United States Patent [19]

Vargas-Gutierrez et al.

[11] Patent Number: 5,482,731
[45] Date of Patent: Jan. 9, 1996

[54] METHOD FOR BONDING A CALCIUM PHOSPHATE COATING TO STAINLESS STEELS AND COBALT BASE ALLOYS FOR BIOACTIVE FIXATION OF ARTIFICIAL IMPLANTS

[75] Inventors: Gregorio Vargas-Gutierrez; Manuel Mendez-Nonell; Juan Mendez-Nonell; Armando Salinas-Rodriguez, all of Saltillo, Mexico

[73] Assignee: Centro de Investigacion y de Estudios Avanzados Del IPN, Mexico

[21] Appl. No.: 235,271

[22] Filed: Apr. 29, 1994

[51] Int. Cl.$^6$ ................................................. A61F 2/28
[52] U.S. Cl. .................... 427/2.27; 427/252; 427/376.7; 427/380; 427/405; 205/191; 204/180.2; 204/181.5
[58] Field of Search ................ 427/2, 252, 2.26, 427/2.27, 380, 405, 376.7; 205/191, 224, 227, 229, 917; 204/181.5, 180.2

[56] References Cited

U.S. PATENT DOCUMENTS

| | | | |
|---|---|---|---|
| 3,294,654 | 12/1966 | Norman et al. | 427/252 |
| 3,589,935 | 6/1971 | Brill-Edwards et al. | 427/252 |
| 4,125,442 | 11/1978 | Rogers | 427/405 |
| 4,770,943 | 9/1988 | Hakamatsuka et al. | 427/380 |
| 4,794,023 | 12/1988 | Shimamune et al. | 427/380 |
| 4,818,572 | 4/1989 | Shimamune et al. | 205/224 |
| 4,882,196 | 11/1989 | Shimamune et al. | 427/2 |
| 4,990,163 | 2/1991 | Ducheyne et al. | 427/2.27 |
| 5,068,122 | 11/1991 | Kokubo et al. | 427/2 |
| 5,104,410 | 4/1992 | Chowdhary | 427/2 |
| 5,112,654 | 5/1992 | Claar | 427/201 |
| 5,178,901 | 1/1993 | Toriyama et al. | 427/2 |
| 5,205,921 | 4/1993 | Shirkanzadeh | 427/2 |
| 5,258,044 | 11/1993 | Lee | 427/2 |

Primary Examiner—Diana Dudash
Attorney, Agent, or Firm—Laurence R. Brown

[57] ABSTRACT

This document discloses a method for bonding a calcium phosphate coating to stainless steels or cobalt base alloys for bioactive fixation of artificial implants. The method consists essentially of the following successive steps: applying and thermally diffusing a layer of titanium or its alloys into the stainless steel or cobalt base alloy substrates, applying a calcium phosphate coating and thermally diffusing $Ca^{2+}$ and $PO_4^{-3}$ ions of the calcium phosphate into the intermediate layer of the titanium or its alloys and finally, the hydrothermal processing of the calcium phosphate coating.

12 Claims, 1 Drawing Sheet

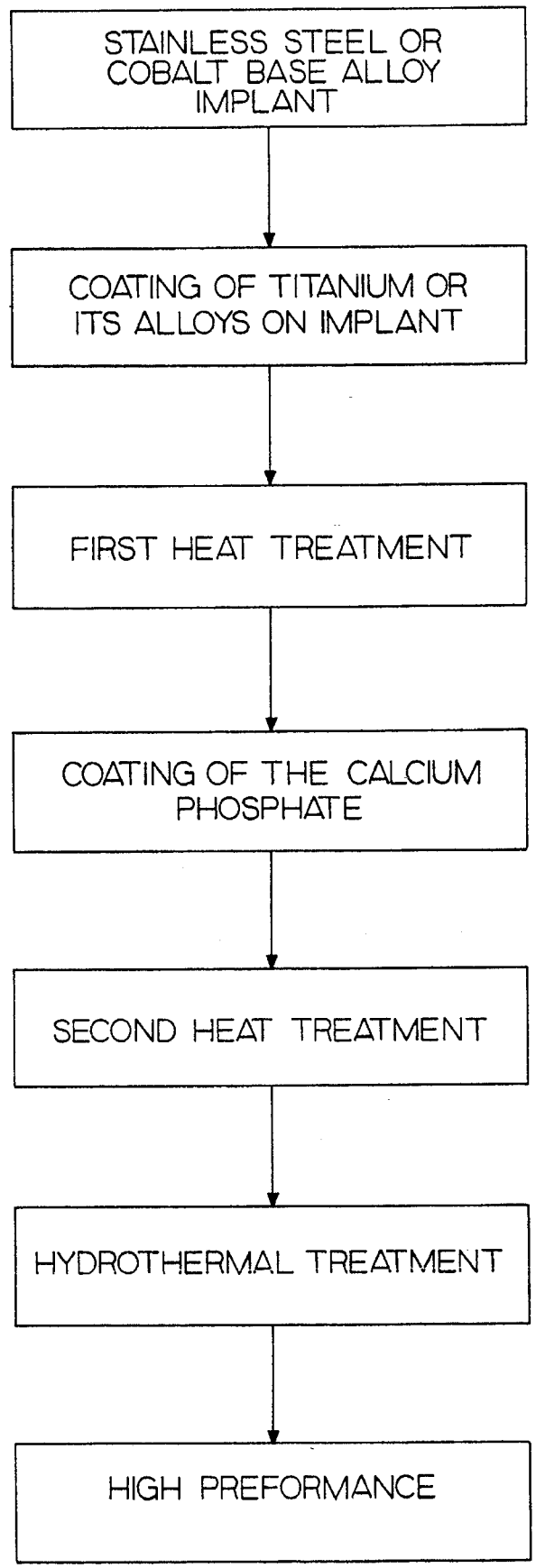

METHOD FOR BONDING A CALCIUM PHOSPHATE COATING TO STAINLESS STEELS AND COBALT BASE ALLOYS FOR BIOACTIVE FIXATION OF ARTIFICIAL IMPLANTS

BACKGROUND OF THE INVENTION

Metallic biomaterials with good wear and mechanical properties for implants are commercially available.

These materials can be readily processed to manufacture orthopaedic implants such as hip and knee replacements. Although these implants possess adequate compatibility with human tissue and have a long history of success in joint arthroplasty, there still remains the problem of fixation to the osseous tissue.

A prerequisite for success of any orthopaedic arthroplasty is achieving permanent fixation of the components of the prosthetic device to the surrounding bony environment with no intervening soft tissue. This process, commonly known as osseointegration occurs at the interface between the bone and the implant surfaces. Osseointegration is affected by biomechanical forces and biomaterial properties. The forces transmitted between the prosthesis and the bone depend on the design and geometry of the implant, the materials used, and the mechanical characteristics of the surrounding bone. The biomaterial properties of the surface determine the relative biocompatibility of the material, surface biochemistry, and therefore, the degree of fixation. Among the materials currently in use for implant fixation, commercially pure titanium and hydroxyapatite (HA) most easily achieve osseointegration.

HA and other calcium phosphate coatings have been shown to be effective in clinical applications due to the strong adherent interface formed with the Ti alloy. The most popular method of applying ceramic coatings to metallic substrates is by the plasma spray process. The bond strength of plasma sprayed HA coating on Ti alloy substrates is mainly derived from the combination of mechanical interlocking with the underlying roughened substrate and the chemical bonding that occurs with the $TiO_2$ layer present on the surface of the substrate. The chemical bonding is believed to occur as a result of the incorporation of $Ca^{2+}$ and $P^{5+}$ ions into the $TiC_x$ films.

At present, the most commonly used metallic alloy employed to fabricate orthopaedic implants for joint arthoplasty is the ASTM-F75 Co-base alloy Co—27Cr—5Mo—0.3C. Processing of this alloy is carried out by investment casting which presents important economic advantages over the processing techniques employed for implants manufactured from Ti and its alloys.

Fixation of Co-base implants is achieved mainly using polymethyl methacrylate bone cement or by applying a metallic porous coat of Co on the surface of the prosthesis. This coating is applied by sinter-annealing the prosthesis covered with small balls of Co on the surface of interest. In this case, the porosity allows mineralized bone to grow into the porous surface, thus achieving a morphological microinterlock. However, there is no chemical bonding of the metal to the bone, and histologic studies of retrieved porous hip and knee prosthesis have shown variable ingrowth. Hydroxyapatite coating on Co-base alloy prosthesis have not shown the same degree of success as in Ti-base alloy implants.

In Cobalt base alloys, the interdiffusion of $P^{5+}$ or $(PO_4)^{3-}$-ions can occur in the passive coating of $Cr_2O_3$. However, the absorption of $Ca^{2+}$ necessary for effective biological osseointegration on the implant surface does not occur in these materials. In addition, $TiO_x$ is thermodynamically more stable than the $Cr_2O_3$ formed on cobalt base alloys.

On the other hand, the extremely high temperatures involved during the plasma spraying causes the HA to melt in the presence of air. This problem is associated to the structure and composition of the resulting coating. Radin and Ducheyne, reported that plasma sprayed HA coatings retain the basic apatitic structure but were devoid of hydroxyl groups. In addition, several other calcium phosphate phases not present in the starting powder were identified in the plasma sprayed coatings.

These phases include β-tricalcium phosphate(TCP), a-tetracalcium phosphate, and oxihydroxyapatite, as well as non-crystalline calcium phosphate material. Because each calcium phosphate phase has different degree of biocompatibility, it is very important to control the formation of crystalline hydroxyapatite to avoid the total reabsorption of the calcium phosphate coatings into the living tissue.

SUMMARY OF THE INVENTION

The present invention provides a method to create a strongly bonded interface between a calcium phosphate coating on a stainless steel or cobalt base alloy substrate, using an intermediate layer of titanium or its alloys. This intermediate layer will be chemically bonded to both, the stainless steels or cobalt base alloys implant, and the calcium phosphate coating.

The present invention also includes a hydrothermal treatment designed for the coated implants to control the formation of non-desired calcium phosphate phases, the degree of HA crystallinity, and the reincorporation of the hydroxyl groups lost during previous processing. The present invention will also provide a better osseointegration mechanism for stainless steels and for Co-base prosthetic implants, improving the biocompatibility of the devices with the human osseous tissue.

BRIEF DESCRIPTION OF THE DRAWINGS

The drawing is a block flow diagram illustrating the sequence of method steps in an invention embodiment.

DESCRIPTION OF THE PREFERRED EMBODIMENTS

The present invention includes the five-step process depicted schematically in the drawing. The first step is the application of a layer of titanium or its alloys to the stainless steels or cobalt base alloys. In order to provide a long life strong adherent layer, a chemical bond must be involved. To achieve this, the diffusion mechanism of the titanium or its alloys into the stainless steels or into the cobalt base alloys plays a very important role. Although it is not mandatory, methods like pack diffusion, thermal spraying, chemical vapor deposition, physical vapor deposition, ion plating, sputtering, electroplating or electrophoresis, followed by a heat treatment which is the second step of the process, can be used to ensure good interdiffusion of titanium and its alloys into the stainless steel or cobalt base matrix. The third step of the method consists in applying the calcium phosphate coating.

Various methods can also be used to assure the interdiffusion of the $PO_4^{-3}$ and $Ca^{+2}$ ions of the calcium phosphate coating into the intermediate layer of titanium, for example: electrophoretic deposition, thermal spraying, frit enamelling, pack cementation, etc. The calcium phosphate coating is then followed by a second heat treatment, which is the fourth step of the process, and ensures the interdiffusion of the $PO_4^{-3}$ and $Ca^{+2}$ into the titanium substrate. The last step of the process involves a hydrothermal treatment. Another embodiment of the invention can be obtained if the last step shown in the drawing is eliminated and the fourth step is performed under a water vapor atmosphere.

What we claim is:

1. A method for bonding a calcium phosphate coating to stainless steel and cobalt base alloys for bioactive fixation of artificial implants, consisting essentially of the following successive steps: applying a single layer of titanium or its alloys on a stainless steel or cobalt base alloy substrate to produce an intermediate layer; a first heat treatment to ensure interdiffusion of the titanium or its alloys into the substrate; applying a single layer of said calcium phosphate coating on said intermediate layer; a second heat treatment to ensure the interdiffusion of the calcium phosphate coating into the intermediate layer; and finally subjecting the substrate with said calcium phosphate coating to a hydrothermal treatment.

2. A method according to claim 1, wherein said layer of titanium or its alloys is applied by a pack diffusion process.

3. A method according to claim 1, wherein said layer of titanium or its alloys is applied by a chemical vapor deposition process.

4. A method according to claim 1, wherein said layer of titanium or its alloys is applied by a physical vapor deposition process.

5. A method according to claim 1, wherein said layer of titanium or its alloys is applied by the electrophoretic process.

6. A method according to claim 1, wherein said layer of titanium or its alloys is applied by sputtering.

7. A method according to claim 1, wherein said layer of titanium or its alloys is applied by an electroplating process.

8. A method according to claim 1, wherein said calcium phosphate coating is applied by a thermal spraying process.

9. A method according to claim 1, wherein said calcium phosphate coating is applied by frit enamelling.

10. A method according to claim 1, wherein said calcium phosphate coating is applied by electrophoretic deposition.

11. A method according to claim 1, wherein said calcium phosphate coating is applied by a pack cementation process.

12. A method for bonding a calcium phosphate coating to stainless steel and cobalt base alloys for bioactive fixation of artificial implants, consisting essentially of the following successive steps: applying a single layer of titanium or its alloys on a stainless steel or cobalt base alloy substrate to produce an intermediate layer; a first heat treatment to ensure interdiffusion of the titanium or its alloys into the substrate; applying a single layer of said calcium phosphate coating on said intermediate layer; a second heat treatment to ensure the interdiffusion of the calcium phosphate coating into the intermediate layer and said second heat treatment including treating the substrate having said calcium phosphate coating under a water vapor atmosphere.

\* \* \* \* \*